(12) United States Patent
Seifert et al.

(10) Patent No.: US 7,184,842 B2
(45) Date of Patent: Feb. 27, 2007

(54) MEDICAL ELECTRICAL LEAD ANCHORING

(75) Inventors: Kevin R. Seifert, Forest Lake, MN (US); Timothy G. Laske, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 474 days.

(21) Appl. No.: 10/664,995

(22) Filed: Sep. 17, 2003

(65) Prior Publication Data

US 2005/0033395 A1  Feb. 10, 2005

Related U.S. Application Data

(63) Continuation-in-part of application No. 10/637,160, filed on Aug. 8, 2003.

(51) Int. Cl.
*A61N 1/05* (2006.01)

(52) U.S. Cl. .......................... 607/126; 607/122
(58) Field of Classification Search ............... 607/116, 607/119, 122, 123, 126–128
See application file for complete search history.

(56) References Cited

U.S. PATENT DOCUMENTS

| | | | |
|---|---|---|---|
| 3,244,174 A | 4/1966 | Wesbey et al. | 128/418 |
| 3,474,791 A | 10/1969 | Bentov | 128/418 |
| 3,485,247 A | 12/1969 | Ackerman | 128/418 |
| 3,516,412 A | 6/1970 | Ackerman | 128/418 |
| 4,144,889 A | 3/1979 | Tyers et al. | 128/418 |
| 4,258,724 A | 3/1981 | Balat et al. | 128/785 |
| 4,341,226 A | 7/1982 | Peters | 128/784 |
| 4,490,326 A | 12/1984 | Beroff et al. | 264/328.16 |
| 4,497,326 A * | 2/1985 | Curry | 607/123 |
| 4,633,880 A | 1/1987 | Osypka et al. | 128/642 |
| 4,972,833 A | 11/1990 | Wildon | 128/419 P |
| 5,217,027 A | 6/1993 | Hermens | 128/784 |
| 5,314,463 A | 5/1994 | Camps et al. | 607/129 |
| 5,350,419 A | 9/1994 | Bendel et al. | 607/132 |
| 5,716,392 A | 2/1998 | Bourgeois et al. | 607/132 |
| 5,792,217 A | 8/1998 | Camps et al. | 607/119 |
| 5,851,227 A * | 12/1998 | Spehr | 607/126 |
| 5,871,528 A | 2/1999 | Camps et al. | 607/119 |
| 5,922,015 A | 7/1999 | Schaldach | 607/126 |
| 6,173,206 B1 | 1/2001 | Shchervinsky | 607/132 |
| 6,360,130 B1 | 3/2002 | Duysens et al. | 607/132 |
| 6,370,434 B1 | 4/2002 | Zhang et al. | 607/122 |
| 6,516,230 B2 | 2/2003 | Williams et al. | 607/116 |
| 6,754,536 B2 * | 6/2004 | Swoyer et al. | 607/40 |
| 2002/0072737 A1 | 6/2002 | Belden | 606/34 |

FOREIGN PATENT DOCUMENTS

EP   0 408 358 B2   8/1999

* cited by examiner

*Primary Examiner*—Carl Layno
(74) *Attorney, Agent, or Firm*—Carol F. Barry; Girma Wolde-Michael

(57) ABSTRACT

A lead body of a medical electrical lead includes a distal end, a first elongated insulated conductor extending toward the distal end and a first electrode coupled to the conductor. A second elongated insulated conductor includes a first portion extending within the lead body to the distal end and a second portion extending distally from the distal end of the lead body where it is terminated by a tissue anchor on which a second electrode is mounted; the tissue anchor includes a surface for receiving a push force from an insertion tool, which is adapted to insert the anchor within a segment of tissue such that the first electrode of the lead body is in close proximity to the segment of tissue.

16 Claims, 7 Drawing Sheets

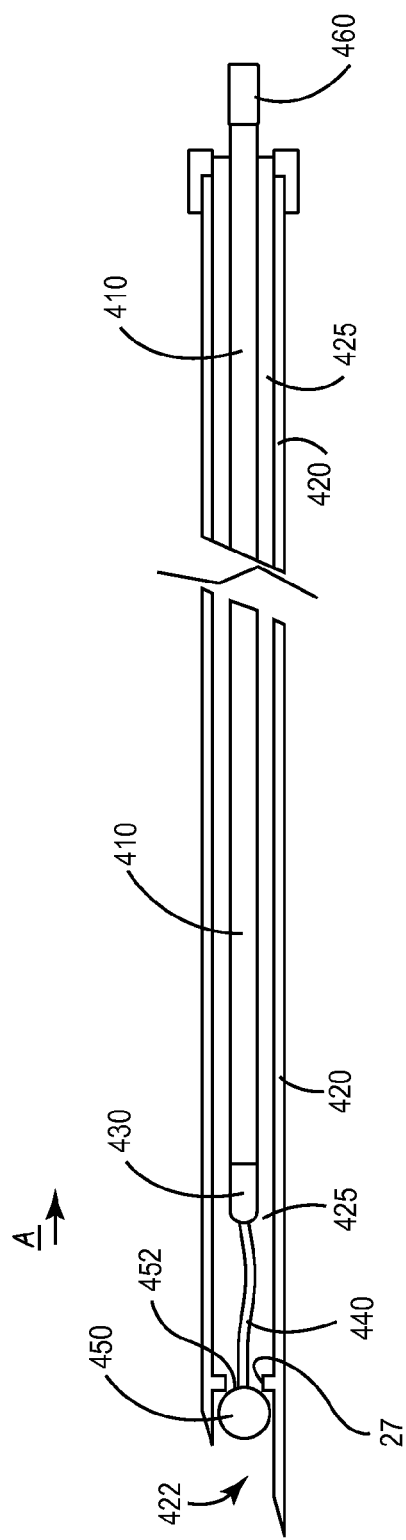
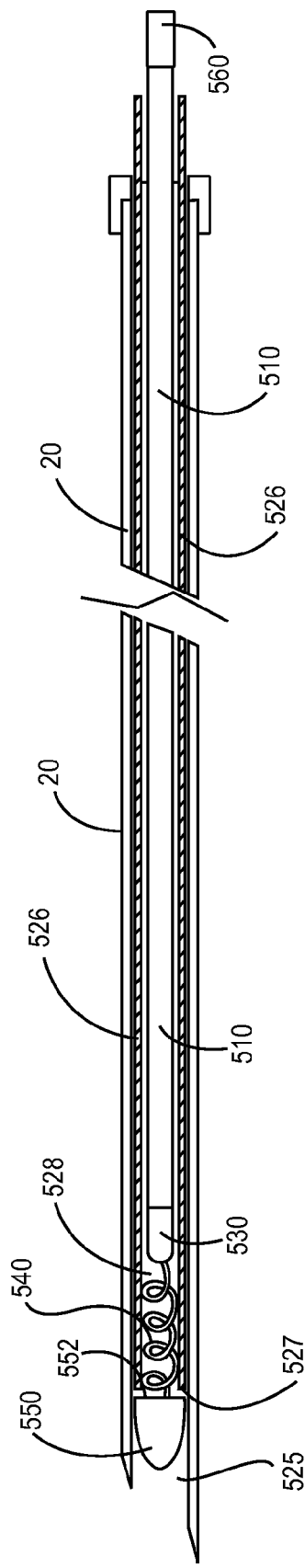

MEDICAL ELECTRICAL LEAD ANCHORING

RELATED APPLICATIONS

This application is a continuation-in-part of application Ser. No. 10/637,160, filed Aug. 8, 2003.

TECHNICAL FIELD

The present invention generally relates to medical electrical leads and more particularly to means for anchoring distal portions of such leads.

BACKGROUND

Electrical stimulation of body tissue and organs is often used as a method of treating various conditions. Such stimulation is generally delivered by means of electrical contact between a pulse generator device and a target site via one or more medical electrical leads connected to the pulse generator device; leads typically include one or more stimulation electrodes joined to a distal portion of the lead, which are positioned and anchored in proximity to the target site. Various lead structures and methods for positioning and anchoring lead electrodes in proximity to target sites have been developed over the years. New structures and methods are necessary to anchor lead electrodes for emerging therapy delivery requirements, examples of which include cardiac resynchronization therapy wherein it may be desirable to implant an electrode in or on myocardial tissue via an epicardial approach. Embodiments of the present invention are described herein in the context of an epicardial implant, however those skilled in the art of implantable medical devices will recognize that embodiments of the present invention may be implemented in a host of other therapy delivery contexts.

BRIEF DESCRIPTION OF THE DRAWINGS

The following drawings are illustrative of particular embodiments of the invention and therefore do not limit the scope of the invention, but are presented to assist in providing a proper understanding. The drawings are not to scale (unless so stated) and are intended for use in conjunction with the explanations in the following detailed description. The present invention will hereinafter be described in conjunction with the appended drawings, wherein like numerals denote like elements, and:

FIG. 4 is a partial section view of a lead and an insertion tool according to alternate embodiments;

FIG. 5 is a partial section of a lead, according to an additional alternate embodiment, and the insertion tool of FIG. 2B;

FIG. 8A is a plan view with partial section views of a bipolar medical electrical lead according to another embodiment of the present invention;

FIG. 8B is a partial section view of the lead shown in FIG. 8A assembled into an insertion tool according to an embodiment of the present invention;

FIG. 9 is a partial section view of a bipolar lead, according to an alternate embodiment, assembled into the insertion tool of FIG. 8B;

FIG. 10 is a partial section view of another embodiment of a bipolar lead within another embodiment of an insertion tool; and FIG. 11 is a partial plan view of yet another embodiment of a bipolar lead and yet another embodiment of an insertion tool according to the present invention.

DETAILED DESCRIPTION OF THE DRAWINGS

The following detailed description is merely exemplary in nature and is not intended to limit the scope, applicability, or configuration of the invention in any way. Rather, the following description provides a convenient illustration for implementing exemplary embodiments of the invention.

Figure 1A:
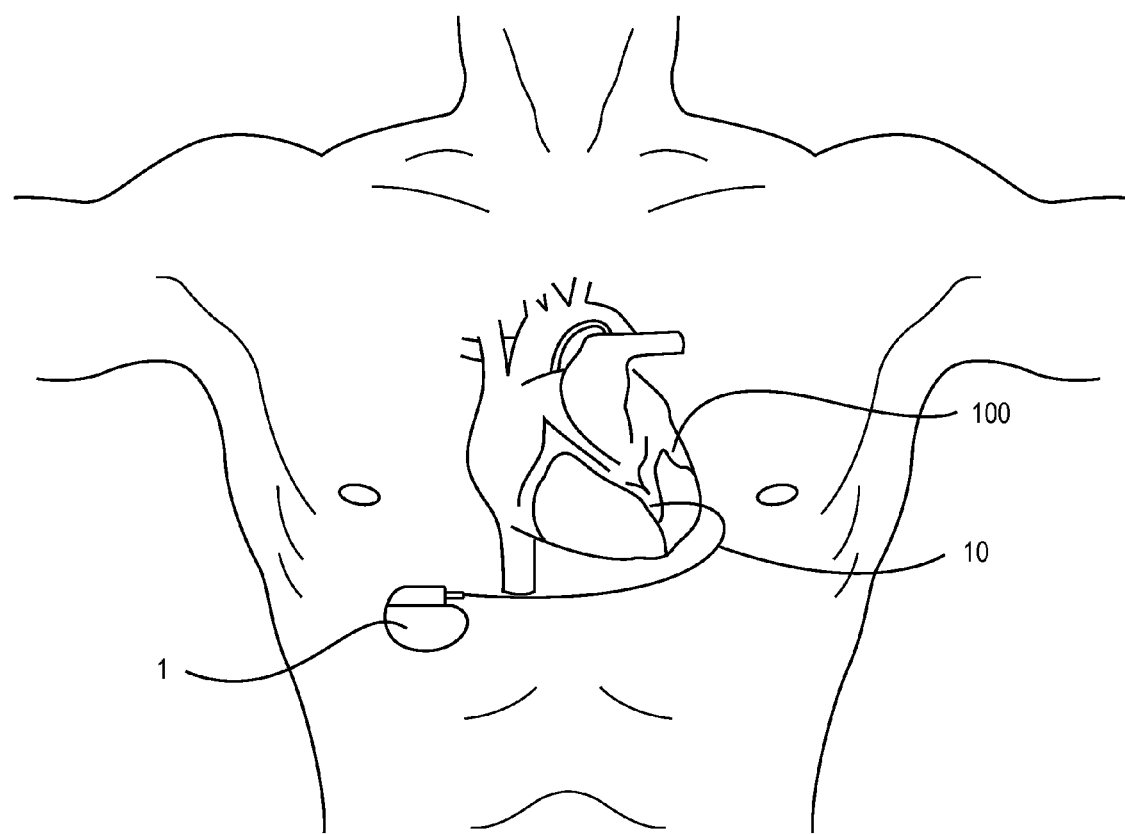
FIG. 1A is a schematic overview of an implantable medical device (IMD) including a medical electrical lead according to embodiments of the present invention.
Figure 1B:
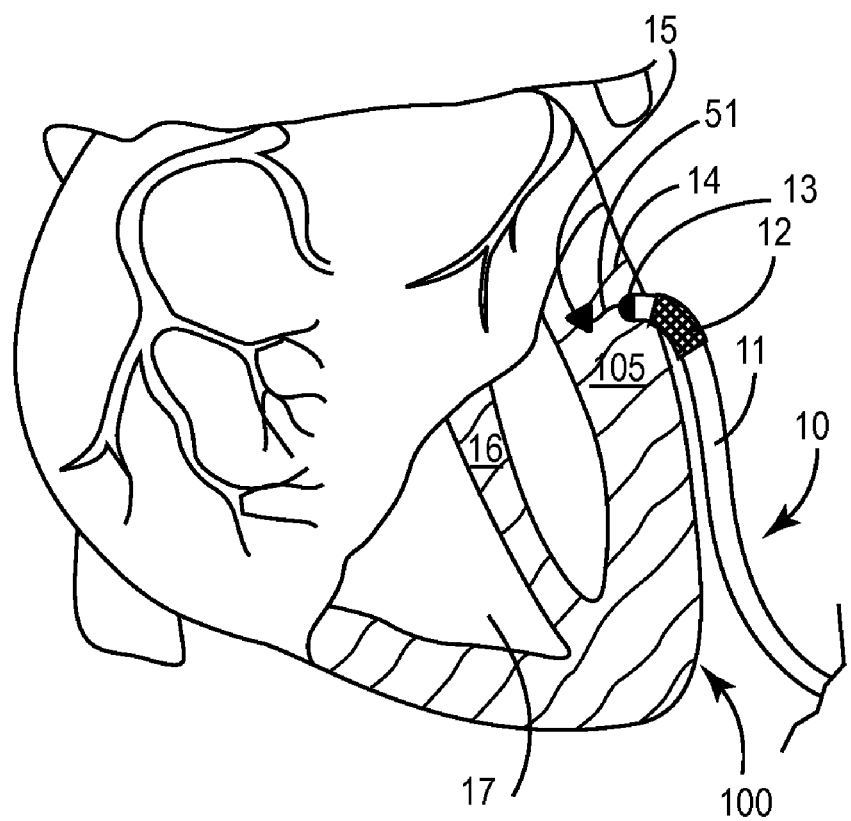
FIG. 1B is an enlarged detail from the schematic overview shown in FIG. 1A.

FIG. 1A is a schematic overview of an implantable medical device (IMD) including a medical electrical lead according to embodiments of the present invention. FIG. 1A illustrates an IMD including an implantable pulse generator (IPG) 1 coupled to a medical electrical lead 10, which in turn is coupled to a heart left side 100 for stimulation thereof. FIG. 1B is an enlarged detail showing salient portions of a distal portion of lead 10. FIG. 1B illustrates lead 10 including an electrode 13 coupled to a lead body 11 and implanted in a wall 105 of left heart 100; electrode 13 is coupled to IPG 1 via a conductor (not shown) extending within lead body to a connector contact (not shown) formed at a proximal end of lead 10, which is connected to IPG 1. According to embodiments of the present invention, as illustrated in FIG. 1B, lead 10 further includes a tissue anchor 15 coupled to lead 10 via a non-rigid tether 14 extending distally from electrode 13; tissue anchor 15 has been pushed into heart wall 105 followed by electrode 13. It should be noted that lead 10 might also be similarly implanted in a septal wall 16 approached from a right ventricle 17 via a transvenous route well known to those skilled in the art, or in any other wall of the heart.

Tissue anchor 15 includes a surface 51 to receive a push force, which will be further described herein below, according to embodiments of the present invention. According to some embodiments, anchor 15 is formed of a bioabsorbable material, examples of which include those taught in lines 10–24 of U.S. Pat. No. 6,173,206. One example of an appropriate bioabsorbable material, polydioxanone is described along with means for molding the material in U.S. Pat. No. 4,490,326, the relevant teachings of which are incorporated by reference herein.

FIG. 1B further illustrates means for promoting chronic adhesion to a surface of heart wall 105 embodied by a layer 120 formed about lead body 11. According to some embodiments of the present invention, layer 120 creates a porous or roughened surface on lead body 11, which encourages tissue ingrowth; examples of such a layer include a polyester mesh sleeve formed about lead body 11.

Figure 2A:
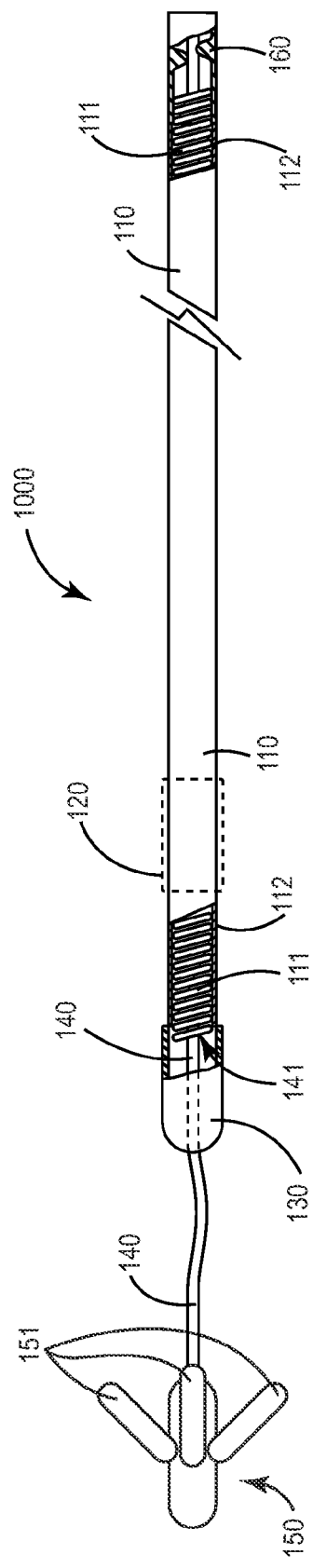
FIG. 2A is a plan view with partial section views of a medical electrical lead according to one embodiment of the present invention.

FIG. 2A is a plan view with partial section views of a medical electrical lead 1000 according to one embodiment of the present invention. FIG. 2A illustrates a lead body 110 including an optional layer 120 (indicated with dashed lines) as means previously described for promoting chronic adhesion, a conductor 111 and an outer insulative sheath 112; conductor 111 couples an electrode 130 to a connector contact 160 for coupling to an IPG, e.g. IPG 1 shown in FIG. 1A. Sheath 112 may be formed of a biocompatible polymer, examples of which include polyurethane and silicone rubber. Materials from which electrode 130 may be formed are well known to those skilled in the art and include platinum, gold, and tantalum; materials from which contact 160 may be formed are likewise known and include stainless steel and titanium; materials from which conductor 111 may be formed are likewise known and include MP35N alloy. Means for coupling conductor 111 to both electrode 130 and connector contact 160 include crimping and welding along with other methods known to those skilled in the art of lead construction.

FIG. 2A further illustrates a tissue anchor 150, including resilient tine members 151, joined to lead body 110 via a non-rigid tether 140 extending distally from electrode 130 according to one embodiment of the present invention. Tine members 151 may be formed from a polymer, for example polyurethane or silicone. Tether 140 and other tether elements described below in conjunction with alternate embodiments are formed from flexible materials, examples of which include, without limitation, nylon thread, polyethylene fiber, liquid crystal polymer fiber, polyester fiber, polypropylene wire, silicone rod or tube and polyurethane rode or tube. In the embodiment illustrated by FIG. 2A, tether 140 also extends through and proximally from electrode 130 through a lumen 141 formed within lead body 110 and is coupled to connector contact 160; thus lead body 110 generally conforms to lead body embodiments taught by Williams and Chivers in U.S. Pat. No. 6,516,230 wherein means for mechanically coupling a fiber cord to lead components are described. Construction methods taught by Williams and Chivers in the '230 patent, incorporated by reference herein, may be used to build embodiments of the present invention, both those wherein a fiber cord extending within lead body is used for a tether and those in which a tether extends only between an electrode and an anchor. In alternate embodiments a conductor is formed as a cable rather than a coil as illustrated in FIG. 2A. Furthermore, another embodiment according to the present invention includes an insulated portion of a cable conductor, which conductor couples electrode 130 to contact 160, extending distally of electrode to form tether 140 joining anchor 150 to lead body 110.

Figure 2B:
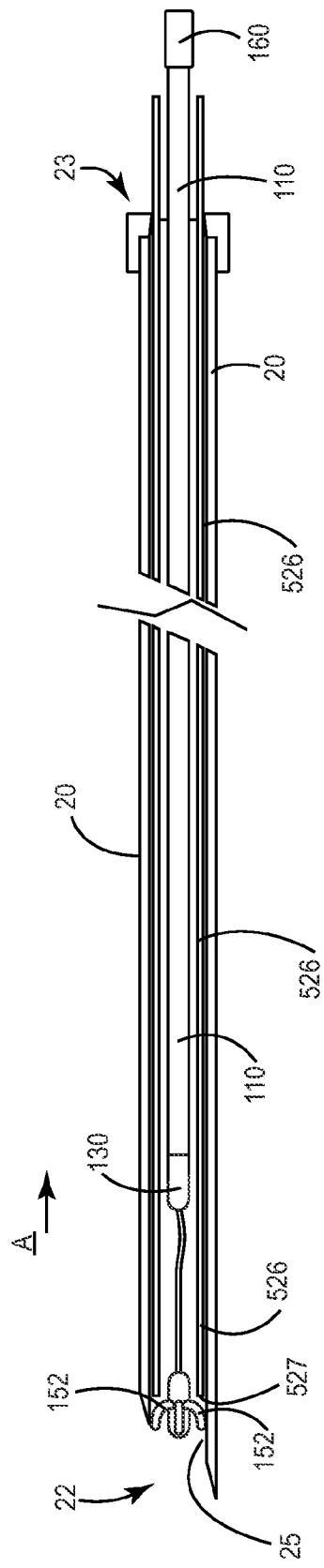
FIG. 2B is a partial section view of the lead shown in FIG. 2A assembled into an insertion tool according to one embodiment of the present invention.

FIG. 2B is a partial section view of lead 1000 assembled into an insertion tool according to one embodiment of the present invention. FIG. 2B illustrates the insertion tool as a needle 20 including a lumen 25 slidably engaging lead 1000, wherein tine members 151 have been folded distally when lead body 110 was pulled, in the direction of arrow A, into needle 20, having been inserted, connector contact 160 first, at a distal end 22 of needle 20. Alternately lead 1000 may be inserted into needle 20 at a proximal end 23 so that tines 151 are folded down in an opposite direction. According to this embodiment of the present invention, undersides 152 of tines 151 are laterally extending surfaces which comprise means for receiving a push force from a distal end 527 of a push tube 526 slideably engaged within lumen 25 of needle 20 and slideably engaged about lead 1000, in order to insert anchor 150 into a segment of tissue at a target site. Needle 20 and push tube 526 are preferably formed from a semi-rigid material, examples of which include, without limitation, a PEEK polymer and a super-elastic metal such as Nitinol.

Figure 3A:
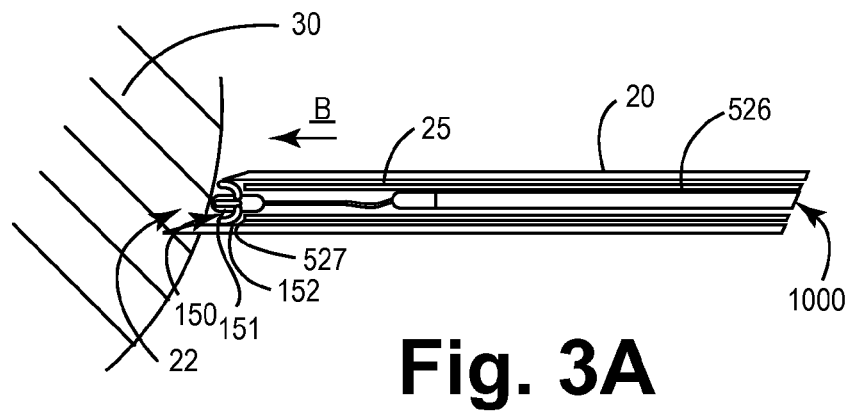
FIGS. 3A–C are schematics depicting implantation of a distal portion of the lead shown in FIG. 2A.
Figure 3B:
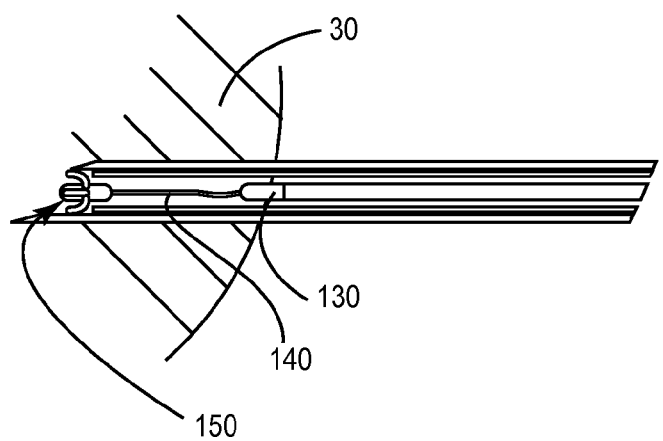
Figure 3C:
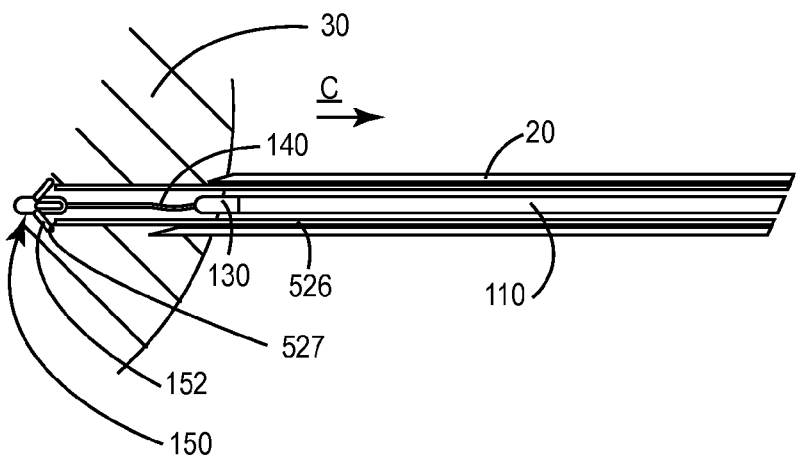

FIGS. 3A–C are schematics depicting insertion of anchor 150 into a segment of tissue 30. For convenience, needle 20 is shown herein having a substantially straight longitudinal axis, however it should be noted that the longitudinal axis of needle 20 may have any curvature facilitating piercing a wall of an organ without risk of perforating that wall, i.e. entry and exit at a same surface of the organ; some such curvatures are taught, in the context of epicardial leads, by Bourgeois et al. in commonly assigned U.S. Pat. No. 5,716, 392. Furthermore, means for gaining access to a target site for insertion of a lead via needle 20 are not illustrated but are well known to those skilled in the art of surgery, either conventional or minimally invasive.

FIG. 3A illustrates lead 1000 carried in lumen 25 of needle 20 as distal end 22 of needle 20 begins to pierce tissue 30. FIG. 3B illustrates needle 20 having carried anchor 150, tether 140 and electrode 130 into tissue 30 and FIG. 3C illustrates a removal of needle 20 over electrode 130 and lead body 110 leaving anchor 150, tether 140 and electrode 130 implanted in tissue 30. As previously described, underside 152 of tine 151 receives a push force from distal end 527 of a push tube 526 slideably engaged within lumen 25 of needle 20; the force, according to arrow B, carries lead 1000 forward in order to implant anchor 150, tether 140 and electrode in tissue 30. It should be noted that a depth of insertion may be varied from that illustrated such that electrode 130 is positioned at a surface 300 of tissue segment 30 rather than within tissue segment 30. Furthermore, although electrode. 130 is described as terminating lead body 110 in the illustrated embodiment, electrode 130 need not terminate lead body 110; according to alternate embodiments an electrode is positioned more proximally along lead body and insertion depth corresponds to the position of the electrode in order to implant electrode in contact with tissue segment 30.

FIG. 4 is a plan view with a partial section of a lead and an insertion tool according to additional alternate embodiments. FIG. 4 illustrates a lead body 410 terminated at a distal end with electrode 430 which is coupled to a connector contact 460 via a conductor within lead body 410 (not shown) and from which extends a non-rigid tether 440 joined to a tissue anchor 450 formed by a substantially spherical member. As with previous embodiments, a laterally extending surface 452 of anchor 450 is means for receiving a push force, however according to the alternate embodiment of an insertion tool, the push force is provided by a protrusion 27 extending into a lumen 425 of a needle 420 which is slideably engaged about lead body 410. In one embodiment, wherein tether 440 is formed from a nylon thread, melting a distal end of tether 440 integrally forms tissue anchor 450. According to the embodiment illustrated in FIG. 4, lead body 410 may be pulled, in the direction of arrow A, into needle 420, having been inserted, connector contact 460 first, at a distal end 422 of needle 420. Of course needle 20 and push tube 526 previously described may also be used as an insertion tool for the lead illustrated in FIG. 4.

FIG. 5 is a partial section of a lead, according to an additional alternate embodiment, assembled within the insertion tool of FIG. 2B. FIG. 5 illustrates a lead body 510 terminated at a distal end with electrode 530 which is coupled to a connector contact 560 via a conductor within lead body 510 (not shown) and from which extends a helically formed non-rigid tether 540 joined to a tissue anchor 550 formed by a substantially conical member. As with previous embodiments, laterally extending surface 552 of anchor 550 is means for receiving a push force provided by distal end 527 of push tube 526 slidably engaged about lead body 510 and slidably engaged within needle 20.

Figure 6:
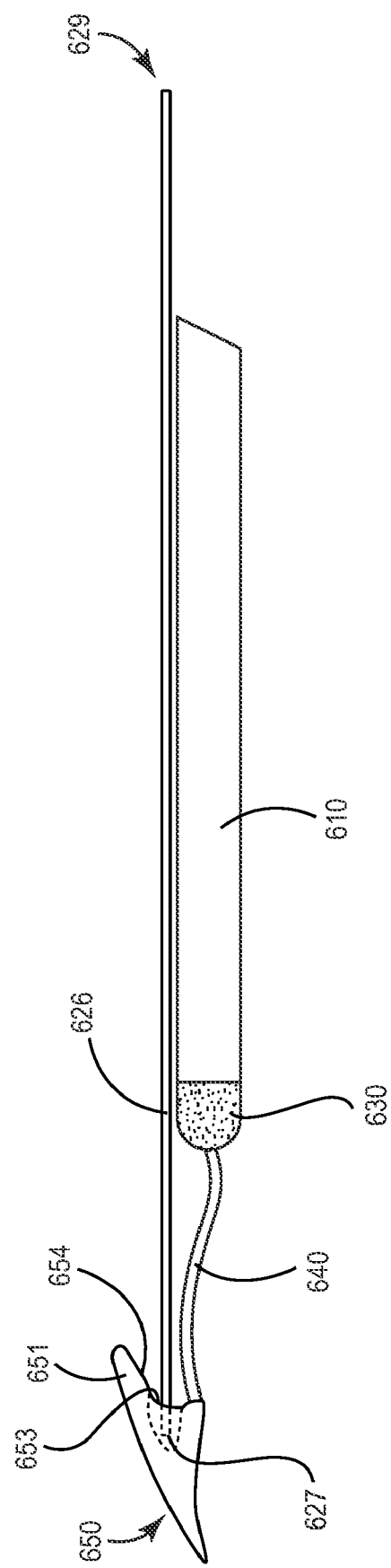
FIG. 6 is a plan view of a distal portion of a lead and an insertion tool according to another embodiment of the present invention.

FIG. 6 is a plan view of a distal portion of a lead and an insertion tool according to another embodiment of the present invention. FIG. 6 illustrates a lead body 610 terminated by an electrode 630 from which extends a tether 640 joined to a tissue anchor 650 including a resilient tine member 651 and a recess 653. According to embodiments of the present invention, FIG. 6 further illustrates recess 653 as means for receiving a push force from a distal end 627 of a stylet insertion tool 626 in order to insert tissue anchor 650 into a segment of tissue thus implanting electrode 630. Alternately, a needle insertion tool, e.g. needle 420, or a push tube within a needle, e.g. push tube 526 within needle 20, may be used to insert anchor 650 by engaging a laterally extending surface 654 of anchor 650 as previously described for other embodiments.

Figure 7:
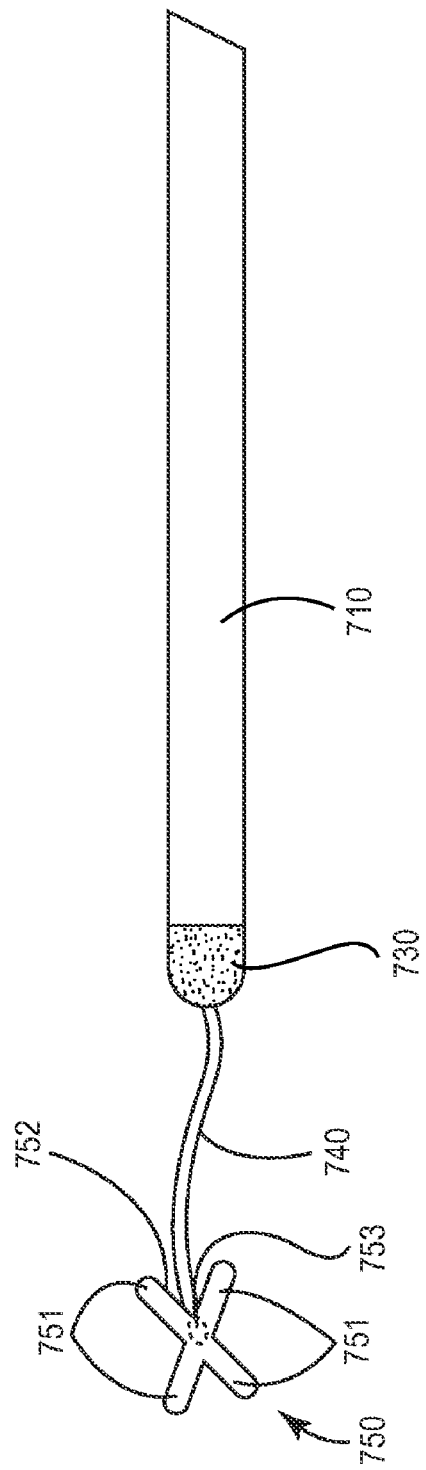
FIG. 7 is a plan view of a lead according to yet another embodiment of the present invention.

FIG. 7 is a plan view of a lead according to yet another embodiment of the present invention. FIG. 7 illustrates a lead body 710 terminated by an electrode 730 from which extends a tether 740 joined to a tissue anchor 750 including resilient tine members 751 and a recess 753. According to embodiments of the present invention, in order to implant electrode 730 by inserting tissue anchor 750 into a tissue segment, recess 753 comprises means for receiving a push force from a stylet insertion tool, e.g. stylet 626 and, according to alternate embodiments, laterally extending surface 752 comprises means for receiving a push force from a needle, e.g. needle 420, or a push tube, e.g. push tube 526.

FIG. 8A is a plan view with partial section views of a bipolar medical electrical lead according to another embodiment of the present invention. FIG. 8A illustrates lead 80 including a first conductor 811 and an outer insulative sheath 812 forming a lead body 810; first conductor 811 couples a first electrode 830 to a first connector contact 860. FIG. 8A further illustrates lead 80 including a second conductor 841 within an inner insulative sheath 842 forming a second elongated insulated conductor 840; second elongated insulated conductor 840 includes two portions, a first portion extending within lead body 810 and second portion extending distally from first electrode 830, which happens to coincide with a distal end of lead body 810 according to the illustrated embodiment, and terminated by a tissue anchor 850, which includes resilient tine members 851 as previously described in conjunction with FIG. 2A. According to embodiments of the present invention, as illustrated in FIG. 8A, a second electrode 835, mounted on tissue anchor 850, is coupled to a second connector contact 865 via second elongated insulated conductor 840 to form a bipolar pair with first electrode 830.

FIG. 8B is a partial section view of the lead shown in FIG. 8A assembled into an insertion tool according to an embodiment of the present invention. FIG. 8B illustrates lead body 810 slidably engaged within lumen 425 of needle 420 having been loaded into distal end 422 of needle 420 per arrow A. As previously described, a push force to insert tissue anchor 850 into a segment of tissue is provided by protrusion 27 extending into lumen 425 of needle 420, and a laterally extending surface 852 of anchor 850 is means for receiving the push. Referring back to FIG. 1B, tissue anchor 850 may be pushed into heart wall 105 such that first electrode 830 is positioned in close proximity to heart wall 105 while second electrode 835, being carried on tissue anchor 850, is implanted within heart wall 105, spaced apart from first electrode 830 to form a bipolar pair for pacing and/or sensing. A means to promote chronic adhesion is also included on lead 80 embodied by a layer 820, as illustrated in FIG. 8A; layer 820 is similar to layer 120 previously described. Referring now to FIGS. 3A–C, needle 420 may be used in a similar fashion to needle 20 and push tube 526 to insert tissue anchor 850 of lead 80.

FIG. 9 is a partial section view of a bipolar lead, according to an alternate embodiment, assembled into the insertion tool of FIG. 8B. FIG. 9 illustrates lead body 910 slidably engaged within lumen 420 of needle 420 and terminated at a distal end by a first electrode 930, which is coupled to a first connector contact 960 via a first conductor (not shown) extending within lead body 910. FIG. 9 further illustrates a second elongated insulated conductor 940, which includes two portions, a first portion (not shown) extending within lead body 910 and second portion extending distally from first electrode 930 and terminated by a substantially spherical member forming a tissue anchor 950. According to embodiments of the present invention, a second electrode 935 mounted on tissue anchor 950 is coupled to a second connector contact 965 via second elongated insulated conductor 940; second electrode 935 is implanted within a segment of tissue by needle 420 wherein protrusion 27 applies a push force to a laterally extending surface 952 of anchor 950.

FIG. 10 is a partial section view of another embodiment of a bipolar lead within another embodiment of an insertion tool. FIG. 10 illustrates lead body 1010 slidably engaged within lumen 525 of needle 20 and terminated at a distal end by a first electrode 1030, which is coupled to a first connector contact 1060 via a first conductor (not shown) extending within lead body 1010. FIG. 10 further illustrates a second elongated insulated conductor 1040, which includes two portions, a first portion (not shown) extending within lead body 1010 and second portion extending distally from first electrode 1030, forming a helix, and terminated by a substantially conical member forming a tissue anchor 1050. According to embodiments of the present invention, a second electrode 1035 mounted on tissue anchor 1050 is coupled to a second connector contact 1065 via second elongated insulated conductor 1040; second electrode 1035 is implanted within a segment of tissue by needle 20 wherein push tube 526, slidably engaged about lead body 1010, applies a push force, via distal end 527, to a laterally extending surface 1052 of anchor 1050.

FIG. 11 is a partial plan view of yet another embodiment of a bipolar lead and yet another embodiment of an insertion tool according to the present invention. FIG. 11 illustrates a lead body 1110 terminated by a first electrode 1130, which is coupled to a first connector contact (not shown) via a first conductor (not shown) extending within lead body 1110. FIG. 11 further illustrates a second elongated insulated conductor 1140, which includes two portions, a first portion (not shown) extending within lead body 1110 and a second portion extending distally from first electrode 1130 and terminated by a tissue anchor 1150; tissue anchor 1150 includes a resilient tine member 1151, a laterally extending surface 1154 and a recess 1153. According to embodiments of the present invention, a second electrode 1135, mounted on anchor 1150, is coupled to a second connector contact (not shown) via second elongated insulated conductor 1140 and is implanted in a segment of tissue via a push force from stylet 626 whose distal end 627 is received within receptacle 1153 of anchor 1150. Alternately, either of needle insertion tools 20/520 or 420 may be used to insertion tissue anchor 1150 by engaging laterally extending surface 1154 of anchor 1150.

In the foregoing specification, the invention has been described with reference to specific embodiments. However, it may be appreciated that various modifications and changes can be made without departing from the scope of the invention as set forth in the appended claims. For example the electrode illustrated terminating a distal end of a lead body may alternately be position proximal to a distal end of the lead body; furthermore the lead bodies described although illustrated as coaxially constructed may take on other forms known to those skilled in the art. Accordingly, the specification and figures are to be regarded as illustrative rather than as restrictive, and all such modifications are intended to be included within the scope of the present invention.

What is claimed is:

1. A medical electrical lead, comprising:
   a hollow needle,
   a flexible lead body within the hollow needle including a distal end, a first elongated insulated conductor extending toward the distal end and a first electrode coupled to the first conductor;
   a second elongated insulated conductor including a first portion extending within the lead body to the distal end and a second portion extending distally from the distal end of the lead body;
   a tissue anchor terminating the second portion of the second conductor and including a surface for receiving a push force from an insertion tool adapted to deploy the anchor from within said hollow needle to engage a segment of tissue such that the first electrode of the lead body is in close proximity to the segment of tissue; and
   a second electrode mounted on the tissue anchor and coupled to the second conductor.

2. A medical electrical lead, comprising:
   a flexible lead body including a distal end, a first elongated insulated conductor extending toward the distal end and a first electrode coupled to the first conductor;
   a second elongated insulated conductor including a first portion extending within the lead body to the distal end and a second portion extending distally from the distal end of the lead body;
   a tissue anchor terminating the second portion of the second conductor and including a surface for receiving a push force from an insertion tool adapted to insert the anchor within a segment of tissue such that the first electrode of the lead body is in close proximity to the segment of tissue; and
   a second electrode mounted on the tissue anchor and coupled to the second conductor;
   wherein the second portion of the second conductor forms a helix in between the distal end of the lead body and the anchor.

3. The medical electrical lead of claim 2, wherein the surface of the anchor extends laterally from the second portion of the second conductor.

4. The medical electrical lead of claim 2, wherein the surface of the anchor forms a recess.

5. The medical electrical lead of claim 2, wherein the anchor comprises a resilient tine member.

6. The medical electrical lead of claim 2, wherein the anchor comprises a substantially spherical member.

7. The medical electrical lead of claim 2, wherein the anchor comprises a substantially conical member.

8. The medical electrical lead of claim 2, further comprising means promoting chronic adhesion of the lead body to the segment of tissue; the means positioned in proximity to the distal end of the lead body.

9. A medical electrical lead, comprising:
   a hollow needle,
   a flexible lead body within the hollow needle including a distal end, a first elongated insulated conductor extending toward the distal end and a first electrode coupled to the first conductor;
   a second elongated insulated conductor including a first portion extending within the lead body to the distal end and a second portion extending distally from the distal end of the lead body;
   a tissue anchor terminating the second portion of the second conductor and including a means for receiving a push force from an insertion tool adapted to deploy the anchor from within said hollow needle to engage a segment of tissue such that the first electrode of the lead body is in close proximity to the segment of tissue; and
   a second electrode mounted on the tissue anchor and coupled to the second conductor.

10. A medical electrical lead, comprising:
    a hollow needle,
    a flexible lead body within the hollow needle including a distal end, a first elongated insulated conductor extending toward the distal end and a first electrode coupled to the first conductor;
    a second elongated insulated conductor including a first portion extending within the lead body to the distal end and a second portion extending distally from the distal end of the lead body;
    a tissue anchor terminating the second portion of the second conductor;
    a second electrode mounted on the tissue anchor and coupled to the second conductor; and
    an insertion tool adapted to push the anchor out of the hollow needle and into a segment of tissue in order to implant the first electrode in proximity to the tissue and the second electrode within the segment of tissue;
    wherein the anchor includes a surface receiving the push from the insertion tool.

11. A medical implant system, comprising:
    a medical electrical lead body including a distal end, a first elongated insulated conductor extending toward the distal end and a first electrode coupled to the first conductor;
    a second elongated insulated conductor including a first portion extending with in the lead body to the distal end and a second portion extending distally from the distal end of the lead body;
    a tissue anchor terminating the second portion of the second conductor;
    a second electrode mounted on the tissue anchor and coupled to the second conductor; and
    an insertion tool adapted to push the anchor into a segment of tissue in order to implant the first electrode in proximity to the tissue and the second electrode within the segment of tissue;
    wherein the anchor includes a surface receiving the push from the insertion tool; and
    wherein the second portion of the second conductor forms a helix in between the distal end of the lead body and the anchor.

12. The implant system of claim 11, wherein the anchor comprises a member selected from the group consisting of a resilient tine, a substantially spherical member, and a substantially conical member.

13. The implant system of claim 11, wherein:
the insertion tool comprises a stylet including a distal end; and
the surface of the anchor forms a recess receiving the distal end of the stylet.

14. The implant system of claim 11, wherein the insertion tool comprises a needle including a lumen adapted to slideably engage the lead body.

15. The implant system of claim 14, wherein the needle further includes a protrusion extending into the lumen and interfacing with the surface of the anchor to push the anchor.

16. The implant system of claim 14, wherein the insertion tool further comprises a push tube slidably engaged within the needle lumen and slidably engaged about the lead body; the push tube including a distal end interfacing with the surface of the anchor to push the anchor.

* * * * *